United States Patent [19]
Davis

[11] Patent Number: 5,586,967
[45] Date of Patent: *Dec. 24, 1996

[54] METHOD AND RECORDING FOR PRODUCING SOUNDS AND MESSAGES TO ACHIEVE ALPHA AND THETA BRAINWAVE STATES AND POSITIVE EMOTIONAL STATES IN HUMANS

[76] Inventor: Mark E. Davis, 21711 Wesley, Apartment D, Laguna Beach, Calif. 92677

[*] Notice: The term of this patent shall not extend beyond the expiration date of Pat. No. 5,352,181.

[21] Appl. No.: 267,149

[22] Filed: Jun. 27, 1994

Related U.S. Application Data

[63] Continuation-in-part of Ser. No. 939,088, Sep. 2, 1992, Pat. No. 5,352,181.
[51] Int. Cl.$^6$ .................................................. A61M 21/00
[52] U.S. Cl. .................................................. 600/28
[58] Field of Search ..................... 600/26–28; 128/731, 128/732, 897, 898

[56] References Cited

U.S. PATENT DOCUMENTS

| | | | |
|---|---|---|---|
| 4,141,344 | 2/1979 | Barbara | 600/28 |
| 4,227,516 | 10/1980 | Meland et al. | 600/26 |
| 4,834,701 | 5/1989 | Masaki | 600/28 |
| 5,123,899 | 6/1992 | Gall | 600/28 |
| 5,135,468 | 8/1992 | Meissner | 600/28 |
| 5,151,080 | 9/1992 | Bick | 600/26 X |

OTHER PUBLICATIONS

Ostrander & Schroeder, Super–Learning, Feb. 1981, pp. 49, 64, 68–69, 114–115, 312–315.

Prevention Magazine, Healthy Pleasures, Jun. 1989, pp. 97–101.

Primary Examiner—Angela Sykes
Assistant Examiner—Stephen D. Huane
Attorney, Agent, or Firm—Walter A. Hackler

[57] ABSTRACT

A method and recording for the use in achieving alpha and theta brainwave states and effecting positive emotional states in humans, is provided which includes a medium having a musical composition thereon with an initial tempo decreasing to a final tempo and verbal phrases recorded in synchrony with the decreasing tempo.

5 Claims, 1 Drawing Sheet

METHOD AND RECORDING FOR PRODUCING SOUNDS AND MESSAGES TO ACHIEVE ALPHA AND THETA BRAINWAVE STATES AND POSITIVE EMOTIONAL STATES IN HUMANS

BACKGROUND OF THE INVENTION

This is a continuation in part of U.S. patent application Ser. No. 07/939,088, filed on Sep. 2, 1992, now U.S. Pat. No. 5,352,181.

The present invention is generally related to a method for producing an audio tape for use in achieving alpha and theta brainwave states and effecting positive emotional states in humans.

It is now known that a human brain operates at various brainwave frequencies. When operating at its highest normal frequencies, between 13 and 25 cycles per minute, the brain is considered to be in the beta state. In the beta state, the brain is excited and active. When operating at 8 to 12 cycles per minute, the brain is considered to be in a relaxed and alert alpha state. Between 4 and 7 cycles per minute, the brain is in the theta state, which is characterized by a restful, meditative condition. Finally, the brain operating at a frequency of 1 to 4 cycles per minute is in the delta state, which is the sleep state.

When an individual's brainwave state is operating in the alpha and theta range, the individual is relaxed and calm. Importantly, an individual's mind is most receptive to learning while in the alpha and theta range. Consequently, the alpha and theta brainwave states are the most conducive to accepting and processing positive messages from an external source.

Human beings often lead stressful lives and it is well known that stress is considered to be a leading contributor to poor health and general unhappiness and in individuals. There is a clearly a need for a system that can safely reduce stress while increasing confidence and enhancing learning ability.

Numerous attempts have been made to influence the emotions of individuals through the use of audiostimuli. Subliminal message systems have been used to implant certain messages and emotions in the mind of a listener. These systems focus on subliminal messages, sometimes combined with a low frequency signal, to create a signal message that is audible only to the subconscious brain. Such a subliminal message system relies on the ability of the subconscious mind to absorb and retain inaudible messages. Furthermore, because the listener is not consciously aware of the particular messages he is receiving, the mysterious nature of subliminal message systems may deter some people from purposefully using the system.

In addition to subliminal message systems, there are numerous self-improvement audio tapes that teach a listener, on a conscious level, how to achieve a positive attitude. However, if the listener's brainwave state is not at its most receptive frequency, the information conveyed may not be remembered or absorbed by the listener.

Attempts have been made to utilize audiosignals for the purpose of directly altering a person's brainwave state. These attempts have employed the use of audiosignals of differing frequencies applied to the ears of a listener. The desired result is that the listener's brain will change its own frequency to match that of the audiosignal. For instance, a low frequency signal will generally cause a listener's initially excited brainwave state to decrease to a lower frequency, more relaxed state. However, a need still remains for a pleasurable, easy to use method of specifically achieving alpha and theta brainwave states and positive emotional states in individuals.

SUMMARY OF THE INVENTION

Accordingly, it is an object of the present invention to provide a method for achieving alpha and theta brainwave states and positive emotional states in individuals. More specifically, the present invention provides a method for producing audio recordings that instill positive emotions in the listener.

As a more specific aspect of the present invention, an original musical composition is developed and instrumentalized, preferably using soft, low dynamic range instruments such as bells, strings or voices. The musical instrumentation is then recorded at specific tempos that purposefully decrease from an initial tempo to a final tempo. The decrease in tempo allows a listener's brainwave state to decrease from a higher to a lower frequency state.

More specifically, the tempo of the music is decreased gradually to achieve the alpha and theta states and the decrease in tempo is virtually imperceptible to the listener. For example, the rate of decrease in tempo will depend on three possible variables: the initial tempo of the music, the length of the musical composition, and the final tempo of the music. Thus, if the initial tempo of the music is at a frequency of about 100 beats per minute and the musical composition is approximately sixty minutes in duration, the rate of tempo reduction may be approximately one beat per minute if a final tempo of about 40 beats per minute is desired. For a shorter musical composition with initial tempo of about 100 beats per minute and final tempo of about 40 beats per minute, the rate of reduction may be as high as approximately 10 beats per minute. Thus, the present invention allows for a variable initial tempo, length of musical composition and rate of reduction of tempo. The desired final tempo is preferably between about 40 and about 60 beats per minute, as this tempo induces the brain to transcend to the alpha and theta states. The effect is that the listener's brain achieves a state that is highly conducive to learning.

A more specific feature of the present invention uses a message system. A script is developed which consists of numerous verbal phrases. The verbal phrases may relate to a central theme, such as learning, self esteem, appreciation of health and feelings of well-being. Each verbal phrase consists of between approximately one and approximately eight words per phrase. The verbal phrases are recorded in synchrony with the musical composition. Preferably, pauses of at least one second in duration are inserted between the phrases. The phrases and pauses are paced to the descending tempo of the musical instrumentation. The object of pacing the verbal phrases and the pauses therebetween is to allow the listener's brainwave state to synchronize with the music and the verbal phrases and thus the brain will be receptive to learning the messages generated by the verbal phrases.

BRIEF DESCRIPTION OF THE DRAWINGS

A better understanding of the present invention may be had by reference to the following description, taken in conjunction with the drawings in which.

DETAILED DESCRIPTION OF THE DRAWINGS

A method and recording for achieving alpha and theta brainwave states and effecting positive emotional states in humans includes, generally, a musical instrumentation system and a message system which are recorded in synchrony with one another.

Figure 1:
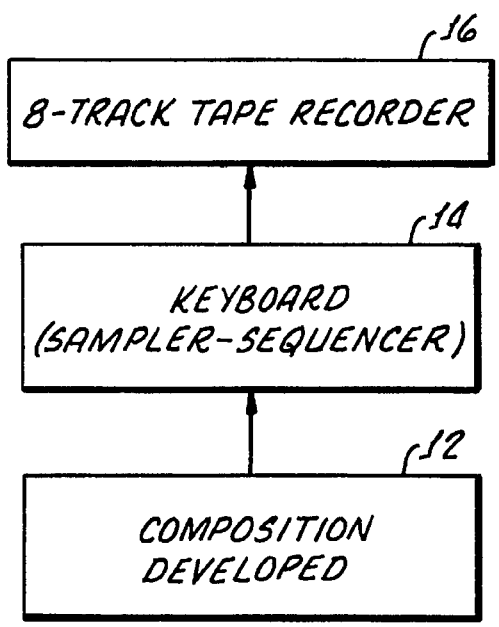
FIG. 1 is a diagram of the development of the musical instrumentation system of the present invention.

As illustrated in FIG. 1, in accordance with the present invention an original musical composition 12 is developed and instrumentalized in soft, low dynamic range instruments such as strings, bells or voices. The composition is the performed on a standard, 16-track, digitized keyboard 14 with a sampler and sequencer. The resulting instrumentation is then fed into an 8-track recorder 16, on one or more of its eight tracks. The initial tempo is recorded at approximately 60 to approximately 120 beats per minute and then, by manual adjustment, it is reduced to a final tempo of approximately 40 to approximately 60 beats per minute. The tempo is preferably decreased smoothly or at regular intervals over the length of the composition 12. The instrumentation is preferably recorded on two tracks of the 8-track recorder 16.

The rate of decrease in tempo depends essentially upon three variables: the length of the composition 12, the initial tempo and the final tempo. The initial tempo is preferably between about 60 and about 120 beats per minute. For example, the listener may desire to listen to the recording when he is in a particularly anxious state of mind. Such a listener may benefit from an initial tempo in the upper range of approximately 120 beats per minute so that his initial brainwave state is matched to the initial tempo of the music. Furthermore, he may require a longer, rather than shorter musical composition in order to gradually reach the desired alpha and theta brainwave states. The purposeful gradual reduction in tempo of the music allows the listener's brainwave state to "lock-in" to the decreasing tempo until a final desired tempo, of between approximately 40 and approximately 60 beats per minute, is reached. The resulting descent in beats per minute is virtually imperceptible and the listener gradually and effectively achieves the desired alpha and theta brainwave states.

Figure 2:
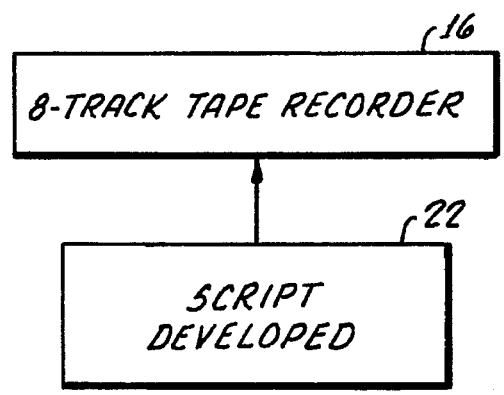
FIG. 2 is a diagram of the development of the message system of the present invention.

FIG. 2 illustrates the message system of the present invention in which a script 22 is developed and recorded on two other tracks of the 8-track recorder. The script 22 is developed around a central theme such as learning, self-esteem or healthy growth. The script is comprised of a plurality of verbal phrases relating to said central theme. More specifically, each verbal phrase is one to approximately eight words in length.

Preferably, the script 22 is read by human readers into an open microphone (not shown) and recorded onto 8-track recorder 16, using two or more of its eight tracks. The script 22 is recorded with pauses between the verbal phrases. Specifically, the pauses have a duration of at least one second in length, and preferably between approximately four and approximately eight seconds in length.

Figure 3:
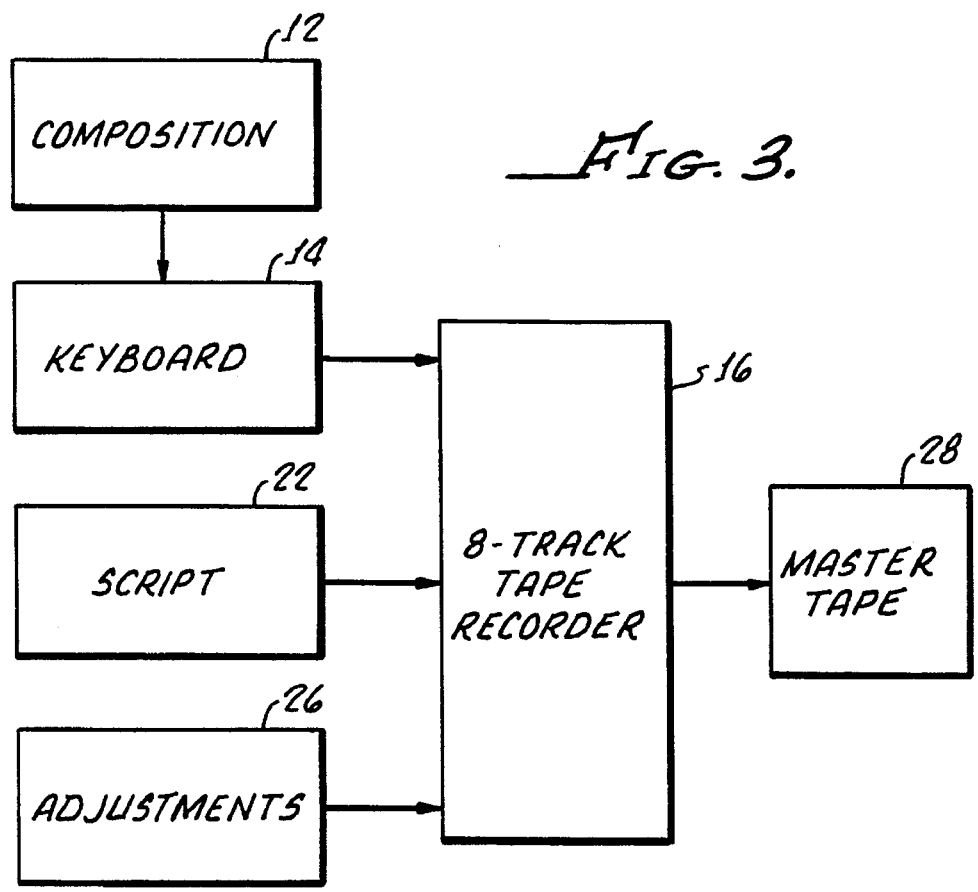
FIG. 3 is a diagram of a preferred embodiment of the present invention in which the musical instrumentation and the message system are combined.

In the preferred embodiment of the present invention, shown in FIG. 3, the instrumentation system and the message system are combined. For the purpose of example only, the 8-track recorder 16 contains two tracks of musical instrumentation and two tracks of recorded verbal phrases. The recorded script 22, consisting of verbal phrases and pauses therebetween, has a tempo that matches the decreasing tempo of the musical instrumentation. For example, if the musical instrumentation has an initial tempo of about 120 beats per minute and a final tempo of about 40 beats per minute, the verbal phrases and pauses therebetween also have initial and final tempos of about 120 and about 40 beats per minute respectively. Preferably, the final tracks of the 8-track recorder contain instrumentation that eliminates all harsh tones and imbalances. The 8-track recorder's tracks, containing instrumentation and script, are then synchronized and adjusted with volume and stereo adjustments 26. The volume and stereo adjustments preferably emphasize the music while allowing the verbal messages to be audible to the listener. A master tape is then produced.

Although there has been hereinabove described a method and recording for achieving alpha and theta brainwave states and positive emotional states in humans, in accordance with the present invention, for the purpose of illustrating the manner in which the invention may be used to advantage, it will be appreciated that the invention is not limited thereto. Accordingly, any and all modifications, variations, or equivalent arrangement which may occur to those skilled in the art should be considered to be within the scope of the invention as defined in the appended claims.

What is claimed is:

1. A method for producing an audio tape for use in achieving alpha and theta brainwave states and effecting positive emotional states in humans to enhance learning and self-improvement, said method comprising:

recording on an audio tape, a musical composition having an initial tempo;

during recording of the musical composition, reducing the initial tempo over a length of the musical composition until a final tempo is reached at an end of the musical composition; and recording on an audio tape, in synchrony with the reducing initial tempo of the musical composition, a plurality of verbal phrases, said verbal phrases being recorded with between one and approximately eight words per phrase, and with pauses between verbal phrases having a duration of between approximately four and approximately eight seconds.

2. The method according to claim 1, wherein the initial tempo is between approximately 60 and approximately 120 beats per minute, and the final tempo is between approximately 40 and approximately 60 beats per minute.

3. The method according to claim 2, wherein the initial tempo is approximately 100 beats per minute, and is reduced at least about one beat per minute, until a final tempo of approximately 40 beats per minute is reached.

4. The method according to claim 2, wherein the initial tempo is approximately 100 beats per minute, and is reduced up to about ten beats per minute, until a final tempo of approximately 40 beats per minute is reached.

5. A recorded audio tape made in accordance with the method of claim 1.

* * * * *